United States Patent [19]

Sugimoto et al.

[11] Patent Number: 4,550,604
[45] Date of Patent: Nov. 5, 1985

[54] ABNORMAL NOISE DETECTOR FOR INSPECTING GEAR UNITS

[75] Inventors: Hiroshi Sugimoto, Toyonaka; Koichi Fukada, Kobe, both of Japan

[73] Assignee: Mitsubishi Denki Kabushiki Kaisha, Japan

[21] Appl. No.: 592,367

[22] Filed: Mar. 22, 1984

[30] Foreign Application Priority Data

Mar. 24, 1983 [JP] Japan ................... 58-50869

[51] Int. Cl.$^4$ ............................................. G01N 29/00
[52] U.S. Cl. ...................................... 73/587; 73/593; 73/659; 73/660
[58] Field of Search .................. 73/593, 587, 660, 659

[56] References Cited

U.S. PATENT DOCUMENTS

| | | | |
|---|---|---|---|
| 2,340,714 | 2/1944 | Traver et al. | 73/593 |
| 3,699,806 | 10/1972 | Weichbrodt | 73/593 |
| 4,352,293 | 10/1982 | Kurihara et al. | 73/593 |
| 4,429,578 | 2/1984 | Darrel et al. | 73/659 |
| 4,437,163 | 3/1984 | Kurihara et al. | 73/593 |
| 4,488,240 | 12/1984 | Kapadia et al. | 73/660 |
| 4,514,797 | 4/1985 | Begin | 73/660 |

*Primary Examiner*—Howard A. Birmiel
*Attorney, Agent, or Firm*—Leydig, Voit & Mayer

[57] ABSTRACT

An abnormal noise detector for detecting abnormal noises produced by a gear unit with an eccentrically mounted gear is disclosed. A first embodiment comprises a microphone placed in the vicinity of a gear unit to be tested, a bandpass filter connected to the microphone which passes only a band of frequencies centered around an integral multiple of the normal fundamental frequency of the noise produced by the meshing of the gears of the gear unit, an amplitude detector which detects the amplitude of the signal from the bandpass filter, a frequency deviation detector which detects the frequency deviation of the signal from the bandpass filter, and recorders for recording the values of the signals from the amplitude detector and the frequency deviation detector as a function of time. A second embodiment comprises a microphone, a digital frequency analyzer and a central processing unit for determining whether abnormalities exist in the data produced by the digital frequency analyzer.

3 Claims, 7 Drawing Figures (a)

(b)

ABNORMAL NOISE DETECTOR FOR INSPECTING GEAR UNITS

BACKGROUND OF THE INVENTION

The present invention relates to an abnormal noise detector for finding flaws in gear units by detecting abnormal noises resulting from these flaws. More particularly, it relates to an abnormal noise detector for gear units having two or more gears which can detect abnormal noises resulting from the rotation of an eccentrically mounted gear.

A conventional method of detecting abnormal noises produced by a gear unit is to employ a microphone and a frequency analyzer. A gear unit to be tested is connected between a drive motor and a load such as a second motor and driven by the drive motor at various speeds. The noise produced by the gear unit is picked up by the microphone which produces an electrical output signal, and the electrical output signal of the microphone is then provided to the frequency analyzer as an input signal. The frequency analyzer samples the signal from the microphone for a certain period of time T and produces a sound pressure level spectrum representing the average sound pressure level of each frequency of noise produced by the gear unit during the sampling period T at the given rate of rotation. By comparing the sound pressure level spectrum for the gear unit being tested with a standard sound pressure level spectrum for a gear unit operating normally, it is possible to detect certain abnormalities in the sound level spectrum due to flaws in the gear unit being tested.

However, this method of detecting abnormal noises is not appropriate for detecting the abnormal noises produced by a gear unit with an eccentrically mounted gear. When two gears mesh, they produce noises having frequencies proportional to the rate at which the teeth of the two gears mesh. If both gears are properly mounted on their geometric centers, the teeth of the two gears will mesh at a constant rate, and the frequency of the noise produced and the sound pressure level of the noise at this frequency will be constant. However, if one of the gears is eccentrically mounted, i.e. due to either a manufacturing imperfection or a bent shaft the center of rotation of one of the gears is not the geometric center of that gear, the rate at which the teeth of the two gears mesh will not be constant, and an abnormal noise will be produced. Rather than being constant, both the frequency and the sound pressure level of the noise produced by the meshing of the gears will vary sinusoidally over time.

This phenomenon will be explained in more detail with reference to FIGS. 1 and 2 of the attached drawings. FIG. 1 is a schematic drawing of a gear unit comprising a first gear 1 and a second gear 2. The first gear has a geometric center 3 and a center of rotation 4, which is displaced from the geometric center 3 by a distance r. The radius of the pitch circle 5 of the first gear 1 is R. The second gear 2 has a geometric center 6 which coincides with its center of rotation.

If both gears were rotating about their geometric centers, the rate at which the teeth of the gears meshed and the fundamental frequency of the noise produced by this meshing would have a constant value of $f_0=(N)(K_1)$, where N is the rate of rotation of the first gear 1 in rotations per second, and $K_1$ is the number of teeth in the first gear 1.

However, since the first gear 1 actually rotates about point 4, the rate at which the gear teeth mesh is constantly changing. A good first order approximation of the instantaneous rate at which the gear teeth mesh and the fundamental frequency of the noise produced by this meshing is given by $$f=(N)(K_1)+(N)(K_1)(r)(\cos(\theta))/R$$

where $\theta$ is the instantaneous angle between the line connecting point 3 and point 4 and the line connecting point 4 and point 6. However, this equation can be reduced to the form $$f=f_0[1+(r)(\cos(\theta))/R]$$

Thus, the rate of meshing of the gear teeth and the fundamental frequency of the noise produced thereby varies sinusoidally over time about a normal value $f_0$. This phenomenon is illustrated in FIG. 2b, which is a graph of the variation over time of the fundamental frequency of the noise produced by the meshing of two gears, one of which is eccentrically mounted.

Similarly, the sound pressure level of the noise due to meshing of the gears varies sinusoidally over time. Since the rate of meshing of the gears is constantly changing, the second gear 2 is continually being accelerated or decelerated by the first gear 1. If the second gear 2 is connected to a load having great inertia, the variation in torque which must be transmitted to the second gear 2 in accelerating or decelerating it causes the sound pressure level of the noise due to meshing to vary sinusoidally about the sound pressure level which would be produced if the gears were meshing at a constant rate. This phenomenon is illustrated in FIG. 2a, which shows the sound pressure level as a function of time for one of the frequencies of noise produced by meshing of the teeth of the gears 1 and 2.

As mentioned above, the conventional method of abnormal noise detection using a frequency analyzer is unsuitable for detecting these abnormal noise phenomena. Namely, if the sampling period T of the frequency analyzer is very short (less than 1/10 of the period of rotation of the first gear 1), even if the sampling is well timed, there is no certainty of detecting the phenomena illustrated in FIG. 2. Conversely, if the sampling period T is made long, since the frequency and sound pressure level vary about constant, normal values, the variations in frequency and sound pressure level tend to be averaged out, and it is difficult to ascertain noise abnormalities from the resulting data.

SUMMARY OF THE INVENTION

It is therefore the object of the present invention to provide an abnormal noise detector for inspecting gear units which can reliably detect noise abnormalities caused by an eccentrically mounted gear in a gear unit.

An abnormal noise detector according to the present invention is constructed so as to continuously monitor the amplitude and the frequency of the noise produced by the meshing of the gears of a gear unit being tested. Since monitoring is carried out continuously, there is no chance of abnormal variations in these phenomenon being overlooked because of a short sampling period T or averaged out because of a long sampling period T as in the conventional method using a frequency analyzer.

An abnormal noise detector according to the present invention comprises a microphone placed in the vicinity of a gear unit to be tested and a detecting means responsive to the electrical output signal produced by the microphone for detecting the amplitude and the frequency deviation of that component of the signal from the microphone lying within a designated band of frequencies.

In a first embodiment of the present invention, the detecting means comprises a bandpass filter which filters the signal from the microphone and passes only a designated band of frequencies, an amplitude detector which detects the amplitude of the output signal from the bandpass filter and produces a corresponding output, a frequency deviation detector which detects the frequency deviation of the output signal of the bandpass filter from the central frequency of the designated band of frequencies and produces a corresponding output, and recorders which record the outputs of the amplitude detector and the frequency deviation detector as a function of time.

In a second embodiment of the present invention, the detecting means comprises a digital frequency analyzer which analyzes the output signal from the microphone and a central processing unit which evaluates the results of analysis by the frequency analyzer and determines whether noise abnormalities exist.

DESCRIPTION OF THE PREFERRED EMBODIMENTS

Figure 1:
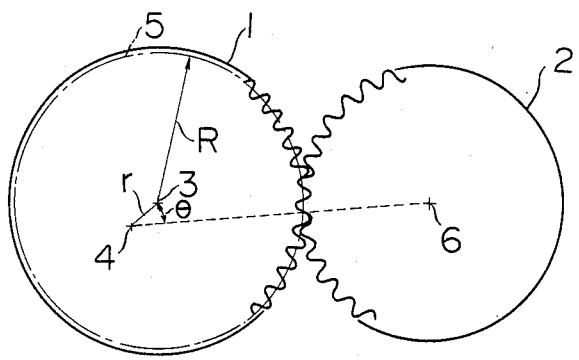
FIG. 1 is a schematic drawing of a gear unit having an eccentrically mounted first gear 1 and a centrally mounted second gear 2.

A first preferred embodiment of an abnormal noise detector according to the present invention will now be described while referring to FIG. 3, which is a block diagram of this embodiment.

In the figure, element number 7 is a gear unit to be inspected for abnormal noise. Although the gear unit 7 may have any number of gears, it will be assumed for simplicity that it contains only two gears. The input shaft of the gear unit 7 is connected to a drive motor 8 for driving the gear unit 7, and the output shaft of the gear unit 7 is connected to a load 9 such as a second motor which is in turn driven by the gear unit 7.

The abnormal noise detector according to the present invention comprises elements number 10 through 16. Element number 10 is a microphone placed in the vicinity of the gear unit 7 for picking up the noise produced thereby during testing and producing a corresponding electrical output signal. Reference number 11 generally indicates a detecting means for detecting the amplitude and the frequency deviation of that component of the signal from the microphone 10 lying within a certain band of frequencies. The detecting means 11 comprises elements number 12 through 16 contained within the dashed line. Element number 12 is an adjustable bandpass filter which is electrically connected to the microphone 10 so as to receive the output signal of the latter as an input signal. Element number 13 is an amplitude detector electrically connected to the bandpass filter 12 so as to receive the output signal from the latter as an input signal. The amplitude detector 13 produces an electrical output signal the level of which is proportional to the instantaneous amplitude of the output signal from the bandpass filter 12. Element number 14 is a first recorder such as an X-Y recorder electrically connected to the amplitude detector 13. The first recorder 14 records the value of the output signal from the amplitude detector 13 as a function of time. Element number 15 is a frequency deviation detector also electrically connected to the bandpass filter 12 so as to receive the output signal from the latter as an input signal. The frequency deviation detector 15 produces an electrical output signal the level of which is proportional to the instantaneous value of the frequency deviation of the signal from the bandpass filter from the central frequency in the band of frequencies passed by the filter 12. Element number 16 is a recorder similar to element number 14 which records the level of the output signal from the frequency deviation detector 15 as a function of time.

Figure 3:
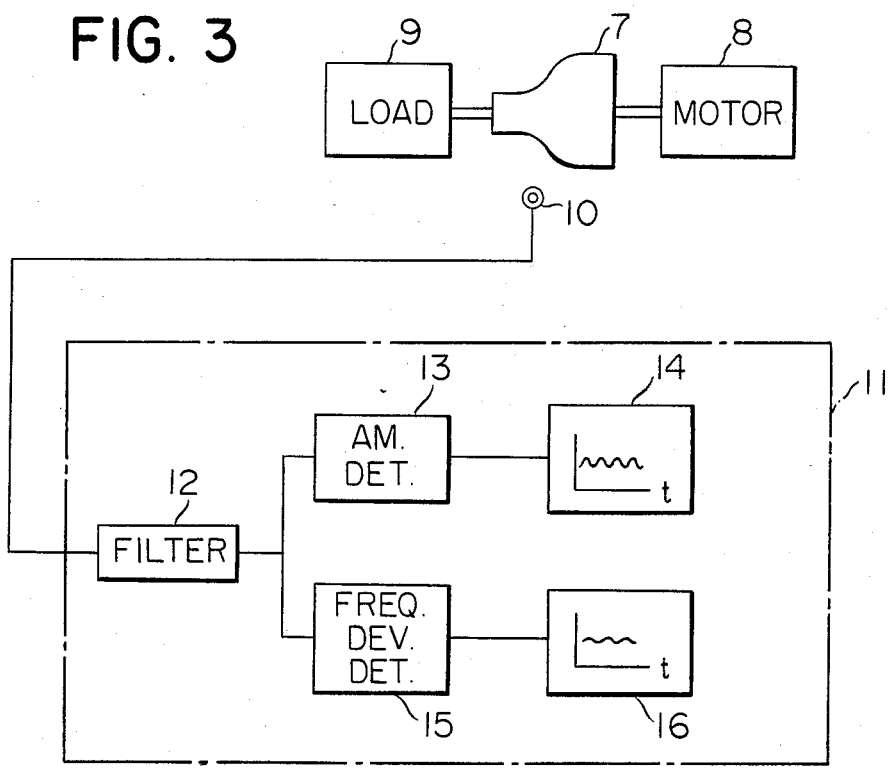
FIG. 3 is a block diagram of a first embodiment of an abnormal noise detector according to the present invention.

The operation of the embodiment shown in FIG. 3 is as follows. When a gear unit 7 is to be inspected, the gear unit 7 is driven at some known rate of rotation N by the drive motor 8, and the load 9 is in turn driven by the gear unit 7. The microphone 10 picks up the noise produced by the gear unit 7 and produces an electrical output signal the amplitude of which is proportional to the sound pressure level of the noise it picks up. The output of the microphone 10 is provided to the bandpass filter 12 as an input signal. The bandpass filter 12 is previously adjusted to pass only a band of frequencies centered around a desired frequency. This desired frequency is some integral multiple of the normal fundamental frequency $f_0$ corresponding to the present rate of rotation N of the gear unit 7, or in other words $(n)(f_o)$, where n is an integer. (Since the rate of rotation N of the gear unit 7 and the number of teeth in each of the gears in the gear unit 7 are known, the fundamental frequency $f_0$ of the noise which would be produced by a normal gear unit can be easily determined.) The output signal from the bandpass filter 12 is provided as input signals to both the amplitude detector 13 and the frequency deviation detector 15.

The amplitude detector 13 produces an output signal the level of which is proportional to the amplitude of the output signal from the bandpass filter 12, and is thus proportional to the instantaneous value of the sound pressure level of the noise produced by the meshing of the gears in the gear unit 7.

The frequency deviation detector 15 produces an output signal the level of which is proportional to the instantaneous value of the frequency deviation from the central frequency of the pass band, $(n)(f_0)$, of the signal from the bandpass filter 12.

The first recorder 14 and the second recorder 16 record the levels of the output signals from the amplitude detector 13 and the frequency deviation detector 15, respectively, as a function of time.

Figure 2:
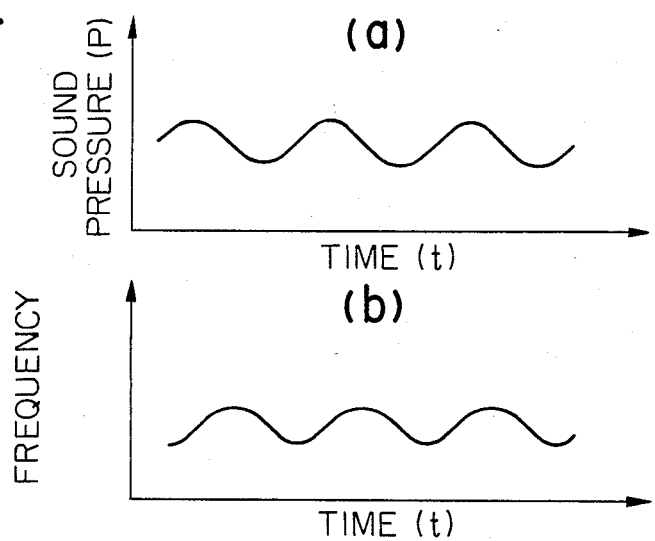
FIG. 2a is a graph of the variation over time of the sound pressure level of a noise produced by the meshing of the gears of FIG. 1.
FIG. 2b is a graph of the variation over time of the fundamental frequency of the noise produced by the meshing of the gears of FIG. 1.

If the gears in the gear unit 7 are properly mounted and rotate about their geometric centers, the output signals from the amplitude detector 13 and the frequency deviation detector 15 will be constant values. However, if one of the gears is eccentrically mounted, the levels of these signals will vary sinusoidally. In this case, if both the first recorder 14 and the second recorder 16 are X-Y recorders, the first recorder 14 will produce a graph of amplitude vs. time like the graph in FIG. 2a, and the second recorder 16 will produce a graph of frequency vs. time like the graph in FIG. 2b. From such graphs, the existence of an eccentrically mounted gear in the gear unit 7 can be easily ascertained. In addition, from the magnitude of the variations of the curves in the graphs, the magnitude of the eccentricity of an eccentrically mounted gear can be estimated.

Figure 4:
FIG. 4 is a block diagram of a second embodiment of an abnormal noise detector according to the present invention.
Figure 5:
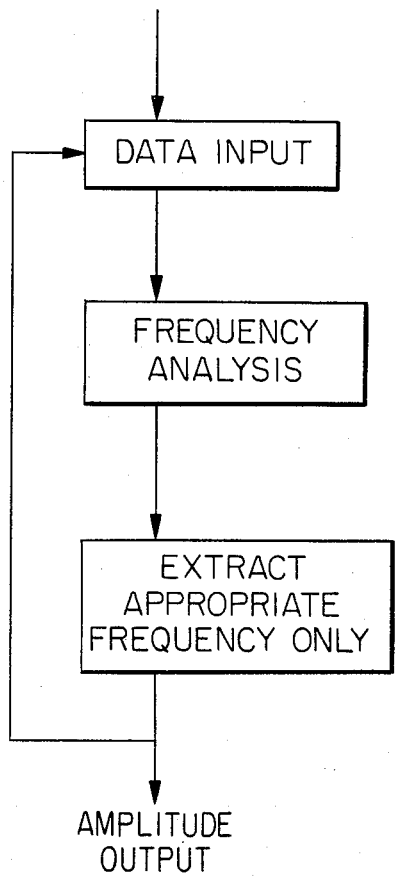
FIGS. 5a and 5b are flow charts illustrating the operation of the embodiment shown in FIG. 4.
Figure 5:
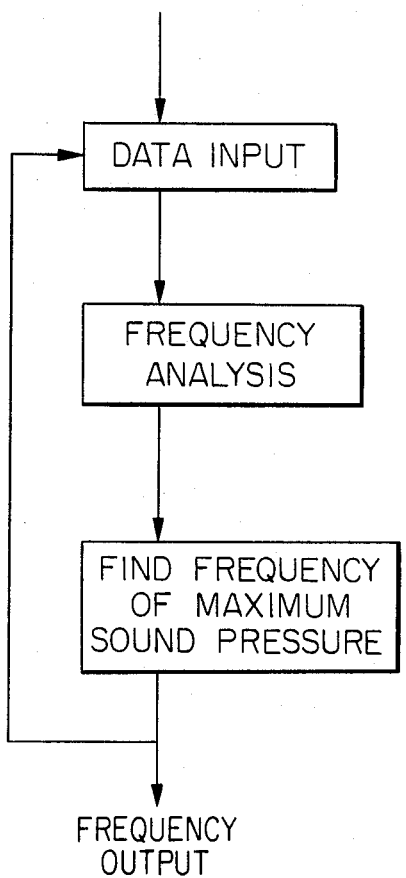

FIG. 4 shows a block diagram of a second embodiment of an abnormal noise detector according to the present invention. In this embodiment, the means for detecting the amplitude and the frequency deviation of that component of the signal from the microphone 10 lying with a certain frequency band comprises elements 17 and 18. Element number 17 is a digital frequency analyzer (a so-called FFT apparatus) electrically connected to a microphone 10. Element number 18 is a central processing unit responsive to the output of the digital frequency analyzer 17 for determining whether there are abnormalities in the data supplied to it by the digital frequency analyzer 17. FIGS. 5a and 5b are flow charts showing the operation of this embodiment. As shown in the flow charts, the digital frequency analyzer 17 outputs data indicating variations with respect to time of the amplitude and frequency of the signals from the microphone 10, and the central processing unit 18 determines the existence of abnormalities in this data.

Although the above embodiments have been described for the case when the gear unit 7 has two gears, the present invention can be applied equally as well to the testing of a gear unit having 3 or more gears.

What is claimed is:

1. An abnormal noise detector for inspecting gear units having gears, two of which mesh and produce noise of a normal fundamental frequency which is a function of the rate at which the teeth of said two gears mesh, comprising:
   a microphone placed in the vicinity of a gear unit to be tested; and
   detecting means responsive to an electrical output signal from said microphone for detecting the amplitude and frequency deviations of said signal from the center frequency within a band of frequencies, the center frequency being an integral multiple of said normal fundamental frequency.

2. An abnormal noise detector as claimed in claim 1, wherein said detecting means comprises:
   filtering means responsive to said signal from said microphone for producing an electrical output signal containing only those components of said output signal from said microphone having frequencies lying within said designated band of frequencies;
   amplitude detecting means responsive to the output signal from said filtering means for producing an output signal the level of which is proportional to the amplitude of the output signal from said filtering means;
   frequency deviation detecting means responsive to the output signal from said filtering means for producing an output signal the level of which is proportional to the frequency deviation of the output signal from said filtering means; and
   recording means for recording the levels of the output signals from said amplitude detecting means and said frequency deviation detecting means as a function of time.

3. An abnormal noise detector as claimed in claim 2 wherein said detecting means comprises:
   a digital frequency analyzer electrically connected to said microphone so as to receive the output signal from said microphone as an input signal; and
   means responsive to the output of said digital frequency analyzer for determining said amplitude and frequency deviations which represent noise abnormalities reflected in the output of said digital frequency analyzer.

* * * * *